United States Patent [19]

Scharfe et al.

[11] 4,104,316

[45] Aug. 1, 1978

[54] PROCESS FOR THE PREPARATION OF 2-CHLOROBUTA-1,3-DIENE

[75] Inventors: Gerhard Scharfe; Rupert Wenzel, both of Leverkusen, Germany

[73] Assignee: Bayer Aktiengesellschaft, Leverkusen, Germany

[21] Appl. No.: 702,834

[22] Filed: Jul. 6, 1976

[30] Foreign Application Priority Data

Jul. 25, 1975 [DE] Fed. Rep. of Germany ....... 2533429

[51] Int. Cl.$^2$ .................. C07C 17/34; C07C 21/20
[52] U.S. Cl. ........................ 260/655; 260/654 D
[58] Field of Search ............... 260/654 D, 655

[56] References Cited

U.S. PATENT DOCUMENTS 3,896,181  7/1975  Brown et al. .................. 260/655
3,936,508  2/1976  Wenzel et al. ................. 260/655

FOREIGN PATENT DOCUMENTS 2,310,744  3/1974  Fed. Rep. of Germany .......... 260/655

*Primary Examiner*—Brian Hearn
*Attorney, Agent, or Firm*—Burgess, Dinklage & Sprung

[57] ABSTRACT

Process for the production of 2-chlorobuta-1,3-diene (chloroprene) which comprises reacting 3,4-dichlorobut-1-ene and sodium butylate in n-butanol to produce a reaction mixture containing the 2-chlorobuta-1,3-diene and sodium chloride in the n-butanol with the sodium chloride being a suspended solid. The reaction mixture is distilled in a distillation column to separate the 2-chlorobuta-1,3-diene as top product and n-butanol having the sodium chloride suspended therein as sump product. The reaction can be performed in the distillation column.

11 Claims, 1 Drawing Figure

U.S. Patent
Aug. 1, 1978
4,104,316
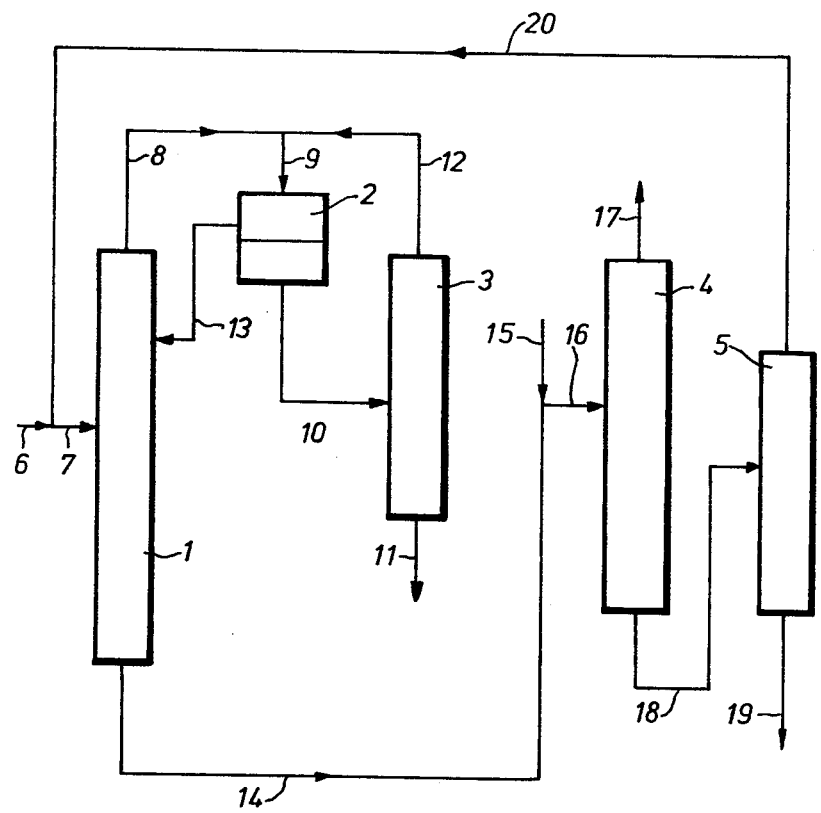

PROCESS FOR THE PREPARATION OF 2-CHLOROBUTA-1,3-DIENE

BACKGROUND

The present invention relates to a process for the preparation of 2-chlorobuta-1,3-diene (chloroprene) by dehydrochlorination of 3,4-dichlorobut-1-ene. It is known from DAS (German Published Specification) 2,310,744 to dehydrate aqueous sodium hydroxide solution azeotropically using n-butanol and to react the solution of sodium butylate in n-butanol, obtained in this way, with 3,4-dichlorobut-1-ene in the liquid phase to give a reaction mixture which essentially consists of chloroprene, n-butanol and suspended sodium chloride. It is further known, from DAS (German Published Specification) 2,310,744, to separate off the solid sodium chloride, formed during the reaction, by mechanical means, for example by centrifuging, and subsequently to remove the chloroprene by distillation from the product which is free from sodium chloride.

THE INVENTION

An improved process for the preparation of 2-chlorobuta-1,3-diene from 3,4-dichlorobut-1-ene and sodium butylate in n-butanol has now been found, which is characterised in that 3,4-dichlorobut-1-ene and a solution of sodium butylate in n-butanol are introduced into a distillation column and reacted, in the distillation column, to give chloroprene and sodium chloride, which is suspended in n-butanol, or that 3,4-dichlorobut-1-ene and a solution of sodium butylate in n-butanol are reacted to give 2-chlorobuta-1,3-diene and sodium chloride, which is suspended in n-butanol, and the resulting reaction mixture is introduced into a distillation column, and that the 2-chlorobuta-1,3-diene, which is formed during the reaction or introduced with the reaction mixture, is separated off as the top product, the sodium chloride being obtained in the suspended form in the sump product which essentially consists of n-butanol.

In order to carry out the process according to the invention, a solution of sodium butylate in n-butanol is first prepared in a manner which is in itself known, for example by dehydrating an aqueous solution of sodium hydroxide by means of n-butanol. The azeotropic dehydration can be so carried out that a binary mixture of n-butanol and water is taken off at the top in a first distillation column, the upper phase obtained after condensation and separation of the layers is returned to the distillation and the lower phase is freed from dissolved n-butanol by stripping in a second distillation column, and the top product from the second column is combined with the top product from the first column. Pure waste water is obtained as the sump product from the second column. The sump product from the first column is the solution of sodium butylate in n-butanol which is required for the reaction with 3,4-dichlorobut-1-ene. The reaction with 3,4-dichlorobut-1-ene is carried out in the liquid phase at temperatures of 0° to 200° C, for example 20° to 60° C, preferably in the absence of molecular oxygen. The process according to the invention can now be carried out using different variants. A common characteristic of all the variants is that the distillation of the reaction mixture obtained from the reaction of sodium butylate/n-butanol and 3,4-dichlorobut-1-ene in order to separate off the chloroprene formed is carried out in the presence of sodium chloride, which is also formed and is in a suspended form. This means that there is, in the distillation column, a suspension of sodium chloride in the reaction mixture or, respectively, in n-butanol, for example on the trays of a bubble tray column or sieve tray column which is used as the distillation unit, this suspension being below the feed point for the sodium butylate/n-butanol solution and for 3,4-dichlorobut-1-ene when the reaction is carried out in a distillation column or below the feed point for the reaction mixture if the reaction is carried out in a separate reaction vessel and the reaction mixture is transferred to a distillation column in order to separate off the chloroprene by distillation. Various embodiments of the process are described below.

The solution of sodium butylate in n-butanol can be reacted with 3,4-dichlorobut-1-ene in the liquid phase in a known manner to give a reaction mixture which essentially consists of chloroprene, n-butanol and suspended sodium chloride and the reaction mixture can then be introduced into a distillation column and there separated by distillation into chloroprene, as the top product, and a sump product which essentially consists of a suspension of sodium chloride in n-butanol. In one variant of the process according to the invention, 3,4-dichlorobut-1-ene and a solution of sodium butylate in n-butanol can be introduced into the distillation column, the reaction to give chloroprene can be carried out in this column and the reaction mixture can be separated by distillation into chloroprene, as the top product, and a suspension of sodium chloride in n-butanol, as the sump product.

It is also possible, during the reaction of sodium butylate with 3,4-dichlorobut-1-ene, which can be carried out, for example, in a stirred kettle or in the sump of a distillation column, partially to distil off — in some cases together with some of the n-butanol — the chloroprene formed during the reaction and then to introduce the residual mixture of chloroprene, n-butanol, suspended sodium chloride and any excess 3,4-dichlorobut-1-ene which may be present into a distillation column and to separate off the chloropene by distillation as the top product and to obtain a suspension of sodium chloride in n-butanol as the sump product.

Furthermore, it is possible first to carry out a substantial conversion of the sodium butylate in n-butanol by means of 3,4-dichlorobut-1-ene and then to introduce the reaction mixture, which in addition to chloroprene, n-butanol and suspended sodium chloride, contains sodium butylate and 3,4-dichlorobut-1-ene which has not yet been converted, into the distillation column and to carry out the further reaction here and, at the same time, to separate off the chloroprene by distillation.

The separation of chloroprene by distillation can be carried out under normal pressure or reduced pressure. Preferably, the distillation is carried out under a reduced pressure of 0.01 to 0.4 bar, for example at 0.06 to 0.3 bar or 0.1 to 0.2 bar, in order to avoid polymerisation of the chloroprene due to a reduced temperature. Inhibitors can be added during the distillation in order to prevent polymerisation of the chloroprene and to increase its storage stability.

It has now been found, surprisingly, that neither mechanical blocking in the column nor deposits in the sump of the column arise during the separation by distillation, which can be carried out, for example, in bubble tray columns or sieve tray columns.

The process according to the invention has the advantage that chloroprene, which can be polymerised easily, is separated off from the reaction mixture, by distillation, directly after it is formed and is obtainable in a pure form. The resulting sump product is virtually completely free from higher-boiling organic compounds, such as, for example, polymers of chloroprene. The sodium chloride which is formed during the reaction is obtained in a very fine-grained form as a suspension in n-butanol. The anhydrous suspended sodium chloride can be separated off from the sump product of the distillation column in various ways. Some of the n-butanol can be taken off as a gas above the sump and, after condensation, obtained in the form of n-butanol which is free from sodium chloride. The sump product can be wholly or partially freed from butanol in an evaporator under normal pressure or reduced pressure. When the process is carried out industrially, the method used can be such that the suspension of sodium chloride in n-butanol is first freed, by distillation, from the bulk, for example from 60 to 90% or 70 to 80%, of the n-butanol and a concentrated suspension of sodium chloride in n-butanol is obtained and that the concentrated suspension of sodium chloride, which is still capable of flow and which contains, for example, 30 to 70% of sodium chloride in n-butanol, is then freed from butanol by distillation, for example in a thin layer evaporator. It is also possible to effect separation of the suspended sodium chloride by mechanical means, for example by filtering or by adding water and converting the sodium chloride into an aqueous solution of sodium chloride.

The reaction of the solution of sodium butylate in n-butanol with 3,4-dichlorobut-1-ene can be so carried out that 1 mol of 3,4-dichlorobut-1-ene is reacted quantitatively with one mol of sodium butylate in n-butanol to give one mol of chloroprene, 1 mol of n-butanol and 1 mol of sodium chloride. The reaction can be carried out under normal pressure, reduced pressure or elevated pressure. Preferably, the reaction is carried out under normal pressure or reduced pressure. For example, pressures of 0.01 to 1 bar can be used. If the reaction is carried out in the distillation column, it is generally carried out under pressures of 0.01 to 0.4, preferably at 0.06 to 0.3 or 0.1 to 0.2, bar. In this case reaction temperatures of about 10°–80° C are employed. A reaction mixture which consists of chloroprene, n-butanol and sodium chloride is obtained. The reaction can also be so carried out that a small excess of 3,4-dichlorobut-1-ene, for example 1.0 to 1.1 mols of 3,4-dichlorobut-1-ene per mol of sodium butylate, is used. In this case, a sump product which, in addition to sodium chloride and n-butanol, still contains small amounts of 3,4-dichlorobut-1-ene is obtained. The 3,4-dichlorobut-1-ene can be separated, in the form of an azeotrope consisting of 3,4-dichlorobut-1-ene and n-butanol and having a boiling point of 113° C, from the n-butanol in this reaction product, before or after the sodium chloride is separated off, and returned to the reaction with the solution of sodium butylate in n-butanol and in this way a n-butanol freed from 3,4-dichlorobut-1-ene can be obtained as a product for recycling for the azeotropic dehydration of the sodium hydroxide solution. It is also possible to work with a less than equivalent amount of 3,4-dichlorobut-1-ene, for example with 0.9 to 1.0 mol of 3,4-dichlorobut-1-ene per mol of sodium butylate. A sump product which, in addition to sodium chloride and n-butanol, still contains small amounts of sodium butylate is then obtained.

In one embodiment of the process, the procedure is such that 1 mol of 3,4-dichlorobut-1-ene is reacted quantitatively with 1 mol of sodium butylate and a suspension of sodium chloride in n-butanol, which is free from sodium butylate and from 3,4-dichlorobut-1-ene, is obtained as the sump product from the column.

In a further embodiment of the process, the procedure is such that 1.0 to 1.1 mols of 3,4-dichlorobut-1-ene are reacted with 1 mol of sodium butylate and that the n-butanol is freed, in a column for low-boiling products, from unreacted 3,4-dichlorobut-1-ene before it is recycled into the azeotropic dehydration.

The reaction in the distillation column is preferably carried out under 10 to 200 mm Hg, for example 50 to 150 or 80 to 120 mm Hg.

One procedure for carrying out the process according to the invention industrially is described with the aid of the accompanying drawing which is a flow sheet for an embodiment of the process.

Concentrated sodium hydroxide solution is introduced via (6), together with a stream of recycled butanol supplied via (20), into a distillation column (1) via line (7). At the top of the column, an azeotrope of n-butanol/water is taken off, at a boiling point of 93° C, via (8) and line (9) and, after condensation in the separator (2), is separated into an upper phase and a lower phase. The lower phase consists of water in which small amounts of n-butanol are dissolved. The lower phase is fed via (10) into the distillation column (3). An azeotrope of n-butanol/water is taken off, via (12), at the top of the column and recycled into (2). The water contained in the feed sodium hydroxide solution and the water of reaction liberated during the conversion of sodium hydroxide to sodium butylate is obtained, in the form of a clean stream of waste water, at the sump of the column (3) and is taken off via (11). A solution of sodium butylate in n-butanol is taken off, via (14) at the sump of the column (1) and fed, together with 3,4-dichlorobut-1-ene (15) via line (16) into the distillation column (4). The invention particularly contemplates distillation column (4) being a multi-zone distillation unit as is provided by a bubble tray or sieve tray column or eaves tray column wherein countercurrent contacting of liquid and gas phases is performed. Such a column can also be a packed column, though bubble trays or sieve trays are preferred. Chloroprene is distilled off under reduced pressure at the top of column (4) and is obtained in a pure form via (17). A suspension of sodium chloride into n-butanol is fed from the sump of column (4) via line (18) into the evaporator (5), where it is separated by distillation into butanol for recycling, which is recycled via (20) into column (1), and solid sodium chloride, which is obtained via (19).

Two streams are introduced into the entire process: concentrated sodium hydroxide solution via (6) and 3,4-dichlorobut-1-ene via (15).

Two end products are obtained: chloroprene via (17) and solid sodium chloride via (19).

In a particular embodiment of the process, the heat of condensation of the top product from column (1) is utilised at 93° C to evaporate the n-butanol in the evaporator (5). The n-butanol vapours thus obtained are brought to a higher pressure and higher temperature by compression and recycled into column (1). This results in advantages with regard to the energy requirements for the entire process.

EXAMPLE 1

The procedure according to the process corresponding to FIG. 1 was employed. A solution of 26.4% of sodium butylate in n-butanol is prepared by azeotropic dehydration of 50% strength sodium hydroxide solution and n-butanol. Per hour, 692 g of this solution are introduced via line (14), together with 238 g of 3,4-dichlorobut-1-ene via line (15), into the centre of a distillation column (4). The distillation column (4) consists of a electrically heated sump with forced circulation and of a stripping section of 1 meter length and 50 mm inner diameter having 20 eaves trays. The rectifying part is a packed column of 2 meter length and 35 mm inner diameter being filled with Raschig rings 4 × 4 mm. The reflux ratio is 10 : 1. Pure anhydrous chloroprene is separated off as the top product under a pressure of 110 mm Hg and at a sump temperature of 75° C. 168 g of chloroprene are taken off per hour via line (17). The sump product from column (4), which consists of a suspension of finely divided sodium chloride in n-butanol, is introduced into an evaporator (5) in which 650 g of n-butanol are recovered, per hour, via line (20). Simultaneously, 111 g of sodium chloride in a solid form are obtained per hour and are taken off via the discharge line (19).

EXAMPLE 2

The procedure followed was as in Example 1. However, the product streams (14) and (15) are not introduced into the distillation column (4) but are fed to a stirred container with a downstream delay tube and there are reacted to give a mixture consisting of chloroprene, n-butanol and suspended sodium chloride, which is then introduced via (16) into the same distillation column (4) as described in Example 1. The pressure of the top of the column is 100 mm Hg, the sump temperature is 72° C. Neither blockages in the column nor deposits in the sump of the column arose during continuous operation of the column for a period of more than 1,000 hours. A fine-grained sodium chloride which was free from organic constituents was obtained from the sump product after removing the n-butanol by distillation in evaporator (5).

What is claimed is:

1. Process for the production of 2-chlorobuta-1,3-diene which comprises contacting 3,4-dichlorobut-1-ene and sodium butylate in n-butanol for formation of a reaction mixture containing said 2-chlorobuta-1,3-diene and sodium chloride in the n-butanol with the sodium chloride being a suspended solid, passing said reaction mixture without having separated off the sodium chloride into a distillation column and therein distilling said reaction mixture to separate the 2-chlorobuta-1,3-diene as top product and n-butanol having the sodium chloride suspended therein as sump product.

2. Process of claim 1, wherein the molar ratio of 3,4-dichlorobut-1-ene to sodium butylate, in said contacting, is 1.0 to 1.1.

3. Process of claim 1, wherein the molar ratio of 3,4-dichlorobut-1-ene to sodium butylate, in said contacting is 0.9 to 1.0.

4. Process of claim 1, wherein n-butanol in the sump product is separated from the sodium chloride in the sump product, and the separated n-butanol is contacted with sodium hydroxide for formation of sodium butylate in n-butanol and employing the so-formed sodium butylate in n-butanol in said contacting.

5. Process of claim 4, wherein unreacted 3,4-dichlorobut-1-ene is present in the sump product, and the unreacted 3,4-dichlorobut-1-ene is separated from n-butanol before said contacting of n-butanol and sodium hydroxide.

6. Process of claim 1, wherein unreacted 3,4-dichlorobut-1-ene is present in the sump product, and the said unreacted 3,4-dichlorobut-1-ene is separated from the suspension of sodium chloride in n-butanol in the sump product.

7. Process of claim 4, wherein the n-butanol is separated from the sump product by distillation.

8. Process of claim 7, wherein the sump product contains unreacted 3,4-dichlorobut-1-ene, and the unreacted 3,4-dichlorobut-1-ene is separated from the sump product before said distillation of n-butanol from the sump product.

9. Process of claim 1, wherein all of the suspended sodium chloride fed into the distillation column is fed below the feed points.

10. Process of claim 1, wherein the distillation is performed in a distillation column with the reaction mixture being fed to an intermediate point of the column, said suspension being present in the column below the feed point.

11. Process of claim 10, wherein all of the suspended sodium chloride in the column is below the feed point.

* * * * *